United States Patent
McMichael

(10) Patent No.: US 11,219,752 B2
(45) Date of Patent: Jan. 11, 2022

(54) TAMPER PROOF CONNECTOR FOR ENTERAL FEEDING DEVICES

(71) Applicant: Avent, Inc., Alpharetta, GA (US)

(72) Inventor: Donald McMichael, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 288 days.

(21) Appl. No.: 16/319,845

(22) PCT Filed: Jul. 14, 2017

(86) PCT No.: PCT/US2017/042050
§ 371 (c)(1),
(2) Date: Jan. 23, 2019

(87) PCT Pub. No.: WO2018/022317
PCT Pub. Date: Feb. 1, 2018

(65) Prior Publication Data
US 2019/0269899 A1 Sep. 5, 2019

Related U.S. Application Data

(60) Provisional application No. 62/368,238, filed on Jul. 29, 2016.

(51) Int. Cl.
*A61M 39/00* (2006.01)
*A61M 39/10* (2006.01)
(Continued)

(52) U.S. Cl.
CPC ...... *A61M 39/1011* (2013.01); *A61M 5/5086* (2013.01); *A61M 39/24* (2013.01);
(Continued)

(58) Field of Classification Search
CPC . A61M 5/5086; A61J 15/0015; A61J 15/0092
See application file for complete search history.

(56) References Cited

U.S. PATENT DOCUMENTS 3,707,972 A 1/1973 Vilari et al.
4,307,903 A 12/1981 Wallace
(Continued)

FOREIGN PATENT DOCUMENTS

JP H 11-155959 A 6/1999
WO WO 03/024519 A1 3/2003

OTHER PUBLICATIONS

International Search Report and Written Opinion for PCT/US2017/042050, dated Oct. 13, 2017, 11 pages.

*Primary Examiner* — William R Carpenter
(74) *Attorney, Agent, or Firm* — Dority & Manning, P.A.

(57) ABSTRACT

An in-line connector for use in an enteral feeding system includes a tamper-proof, single-use connector having a first component connectable to a first feeding device of the feeding system, and a second component connectable to a second feeding device of the feeding system. A releasable locking mechanism is provided such that the first component and the second component do not rotate when connected. The connector further includes one or more prongs positioned substantially flush against an interior wall of the second component when the first component and the second component are connected such that the prongs do not interfere with the releasable locking mechanism. Meanwhile, the one or more prongs are displaced away from the interior wall when the first component is detached or disconnected from the second component such that the second component resists re-insertion or reattachment of the first component.

19 Claims, 6 Drawing Sheets

(51) Int. Cl.
  *A61M 39/24* (2006.01)
  *A61M 39/26* (2006.01)
  *A61M 5/50* (2006.01)
  *A61J 15/00* (2006.01)

(52) U.S. Cl.
  CPC .......... *A61M 39/26* (2013.01); *A61J 15/0015* (2013.01); *A61M 2039/1016* (2013.01); *A61M 2039/1027* (2013.01); *A61M 2039/1077* (2013.01)

(56) References Cited

U.S. PATENT DOCUMENTS

| | | |
|---|---|---|
| 4,338,933 A * | 7/1982 | Bayard ................ A61M 39/14 604/411 |
| 4,344,435 A | 8/1982 | Aubin |
| 4,668,217 A | 5/1987 | Isono |
| 4,826,486 A | 5/1989 | Palsrok et al. |
| 4,873,977 A | 10/1989 | Avant et al. |
| 5,098,405 A | 3/1992 | Peterson et al. |
| 5,251,873 A | 10/1993 | Atkinson et al. |
| 5,344,414 A | 9/1994 | Lopez et al. |
| 5,403,284 A | 4/1995 | Gross |
| 5,540,265 A | 7/1996 | Polaschegg et al. |
| 5,554,140 A | 9/1996 | Michaels et al. |
| 5,713,850 A | 2/1998 | Heilmann et al. |
| 5,803,509 A | 9/1998 | Adams |
| 5,836,924 A | 11/1998 | Kelliher et al. |
| 6,036,171 A | 3/2000 | Weinheimer et al. |
| 6,044,859 A | 4/2000 | Davis |
| 6,045,536 A | 4/2000 | Meier et al. |
| 6,375,231 B1 | 4/2002 | Picha et al. |
| 6,682,508 B1 | 1/2004 | Meythaler et al. |
| 6,808,521 B1 | 10/2004 | McMichael |
| 8,142,418 B2 | 3/2012 | McMichael et al. |
| 9,149,621 B2 | 10/2015 | Bizup |
| 2002/0077604 A1 | 6/2002 | Willis et al. |
| 2002/0099360 A1 | 7/2002 | Bierman |
| 2003/0073971 A1 | 4/2003 | Saker |
| 2005/0087715 A1 | 4/2005 | Doyle |
| 2005/0090805 A1 | 4/2005 | Shaw et al. |
| 2005/0187524 A1 | 8/2005 | Willis et al. |
| 2009/0163892 A1* | 6/2009 | McMichael ........... A61M 39/26 604/533 |
| 2011/0046550 A1* | 2/2011 | Schiller .................. A61M 5/28 604/111 |
| 2012/0016300 A1* | 1/2012 | Ruan .................... A61M 5/002 604/110 |
| 2012/0041426 A1 | 2/2012 | Bizup |
| 2017/0000999 A1* | 1/2017 | Dennis ............... A61M 39/1011 |
| 2017/0009920 A1* | 1/2017 | Canatella ............ F16L 37/0985 |

* cited by examiner

TAMPER PROOF CONNECTOR FOR ENTERAL FEEDING DEVICES

CROSS REFERENCE TO RELATED APPLICATIONS

The present application is the national stage entry of International Patent Application No. PCT/US2017/042050 having a filing date of Jul. 14, 2017, which claims priority to U.S. Provisional Application Ser. No. 62/368,238, having a filing date of Jul. 29, 2016, the entire contents of which are incorporated herein by reference.

BACKGROUND OF THE INVENTION

The present invention relates generally to enteral feeding devices, and more particularly to an in-line connector between components of the feeding system.

It is a known medical procedure to catheterize a patient in order to provide nutritional solutions directly into the stomach or intestines of the patient. A stoma is formed in the stomach or intestinal wall and a gastrostomy or jejunostomy catheter device is placed through the stoma. This device is supplied with a nutritional solution via a tube, adapter, infusion set, or any combination of devices for delivering the nutritional solution for direct injection into a patient's stomach or intestines. This process is referred to as enteral feeding.

To ensure that the gastrostomy or jejunostomy device is maintained in the proper position, it is common to use a retention device (balloon, bumper or catheter pigtail) disposed near the distal (patient) end of a catheter shaft component of the device. Inflating the balloon causes the retention device to contact the anatomical structure (i.e., a duct or stomach wall) and thereby prevent the catheter from moving out of the proper position. Although not required, such gastrostomy or jejunostomy devices may include a "low-profile" head at the proximal end of the catheter shaft. The head, which also helps hold the catheter in place, includes an opening for receiving the feeding solution and a one-way valve for preventing fluids from flowing out of the patient via the catheter. U.S. Pat. Nos. 5,997,503 and 5,997,546 disclose examples of low-profile balloon catheter gastrostomy devices that may be suitable for enteral feeding, and both are incorporated by reference herein for all purposes, although it is to be understood that it is not required that the devices have a balloon or be low-profile.

An enteral feeding adapter is often used to transfer solutions from an upstream source to the gastrostomy device, and the enteral feeding adapter typically includes an elongate tube having a distal end that engages in the head of the gastrostomy device. This tube typically extends at least partially through the device and maintains the one-way valve in the catheter in an open position during the enteral feeding process. The adapter may be connected directly to a feeding tube or to an infusion set that is, in turn, connected to an enteral feeding pump, a drip chamber, or any other mechanism for providing the feeding solution.

One problem associated with this configuration and process is that the feeding tube and feed set adapter may accidentally separate during the feeding process and disrupt the flow of nutritional fluids to the patient. In addition, the nutritional solution and any medicine will spill over the patient. The tube connected to the gastrostomy device provides an open pathway to the patient's stomach, and gastric juices can potentially leak out of the tube, which can result in burns and other complications.

Solutions to this problem have been proposed in the art. For example, U.S. Pat. Nos. 5,057,093; 5,322,073; and 5,554,140 describe interlock devices integrally formed with the feeding devices to secure the components together. Clamping devices are also disclosed in U.S. Pat. Nos. 4,230,109 and 5,248,306. U.S. Pat. No. 6,375,231 discloses another proposed solution wherein a clamp secures a feeding adapter in position relative to a feeding device. The clamp includes C-shaped members integrally connected by elastic webs. One of the members attaches to the feeding adapter, and the other member attached to the feeding device. Elastic bands are used to secure the C-shaped members to their respective components.

Another problem with currently available enteral feeding adapters, such as those including break-away connectors, is that they generally are not tamper proof, and it is possible that the enteral feeding adapters might be reassembled and reused after their initial connection and disconnection, which could result in improper reassembly and malfunctioning of the adapter and which could subject the patient to an increased risk for infection.

The present invention provides a novel solution to the problem of reassembly and reuse of enteral feeding adapters by providing an adapter that is not reusable and cannot be easily reassembled after a single use.

SUMMARY

Objects and advantages of the invention will be set forth in part in the following description, or may be obvious from the description, or may be learned through practice of the invention. The invention will be described in greater detail below by reference to embodiments thereof illustrated in the figures.

An in-line connector is provided for use in an enteral feeding system. The connector is not limited to use with any particular type of enteral feeding system, and may be configured or modified for use as an in-line component with virtually any enteral feeding system. The in-line connector includes a first component connectable to a first feeding device of the feeding system and having an upper end and a lower end a second component connectable to a second feeding device of the feeding system and having an upper end and a lower end; and a releasable locking mechanism configured between the lower end of the first component and the upper end of the second component, wherein in a connected state the first component and the second component define a fluid passage between the first and second feeding devices; wherein an interior wall of the second component defines a recess for receiving the first component, wherein the interior wall includes one or more movable prongs that are substantially flush with the interior wall when the first component and the second component are in a connected state, and wherein the one or more prongs are displaced away from the interior wall when the first component and the second component are in a disconnected state.

In one particular embodiment, the prongs can sit in pockets in the interior wall when the first component and the second component are in a connected state.

In another embodiment, the prongs can be curvilinear when the first component and second component are in a disconnected state. Further, a tip of each prong can curve towards the upper end of the second component when the first component and second component are in a disconnected state.

In still another embodiment, the prongs can have a length that is less than a length of the interior wall.

In yet another embodiment, the prongs can be formed from polyacetal, polycarbonate, acrylonitrile butadiene styrene, co-polyester or a combination thereof.

In another embodiment, the prongs can be spring-loaded.

In one more embodiment, the prongs can prevent reconnection of the first component and the second component after the first component and the second component are in a disconnected state.

In another embodiment, the in-line connector can be single use.

In still another embodiment, the releasable locking mechanism can include one or more tabs present on an outer surface of the first component and one or more corresponding indentations present on the interior wall of the second component. Further, the prongs can be positioned beneath the indentations and towards the lower end of the second component. In addition, the indentations can be positioned above the prongs and towards an upper end of the second component.

In yet another embodiment, the first component can include an elongated body, wherein the upper end of the first component can be configured for receipt of a feeding tube therein and the lower end of the second component is generally cylindrical, further wherein the lower end of the second component can be configured for receipt of a feeding adapter therein and the upper end of the first component defines a cylindrical recess for receipt of the lower end of the first component.

In one more embodiment, the first component and the second component can each further include an automatic shutoff valve configured therein such that in a disconnected state of the first component and the second component, the shutoff valve in the first component can prevent flow out of the first component in a first direction and the shutoff valve in the second component can prevent flow out of the second component in a second direction that is opposite from the first direction, wherein the shutoff valve in the first component can be engaged and moved to an open position by a component in the second end of the second component upon connecting the first component and the second component together.

Further, the shutoff valve in the first component can include a tapered plug member movable within a tapered chamber, where the plug member can further include an engagement nub extending through an opening in the lower end of the first component, wherein the nub can be engaged by a component in the upper end of the second component to move the plug to an open position of the shutoff valve. In addition, the plug member can be moved to a sealed position within the chamber by fluid flow through the first component in the first direction.

Moreover, the shutoff valve in the second component can be biased to a closed position against flow through the second component in the second direction and can be opened by fluid flow through the second component in the first direction.

In still another embodiment, the in-line connector can include a clamping or screw connection mechanism on the first component that can be configured to releasably attach the first component to the first feeding device.

In yet another embodiment, the in-line connector can include a clamping or screw connection mechanism on the second component that can be configured to releasably attach the second component to the second feeding device.

In one more embodiment, an enteral feeding system for delivering a nutritional solution to a gastrostomy feeding device in a patient is provided. The system can include an upstream feeding device, a downstream feeding device, and the in-line connector as discussed above, wherein the in-line connector can be configured between the upstream feeding device and the downstream feeding device.

The present invention also contemplates an in-line connector for use in an enteral feeding system, where the in-line connector includes a first component connectable to a first feeding device of the feeding system and having an upper end and a lower end; a second component connectable to a second feeding device of the feeding system and having an upper end and a lower end; and a releasable locking mechanism configured between the lower end of the first component and the upper end of the second component, wherein in a connected state the first component and the second component define a fluid passage between the first and second feeding devices; wherein an interior wall of the second component defines a recess for receiving the first component, wherein the interior wall includes one or more movable elements that are substantially flush with the interior wall when the first component and the second component are in a connected state, and wherein the one or more movable elements are displaced away from the interior wall when the first component and the second component are in a disconnected state.

Further, the moveable elements can include compressible materials, springs, compressible sponge or sponge-like materials that expand or revert to prevent reinsertion; deformable bands, films or film-like elements, strings, webs or web-like elements that initially separate and then revert to prevent reinsertion; flexible annular rings, annular springs or the like that contract radially to prevent reinsertion and combinations of the above.

It should be readily appreciated that the present invention also encompasses any manner of enteral feeding system incorporating the connector according to the invention as set forth herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention to one skilled in the art, including the best mode thereof, is set forth more particularly in the remainder of the specification, including reference to the accompanying figures, in which.

Figure 1:
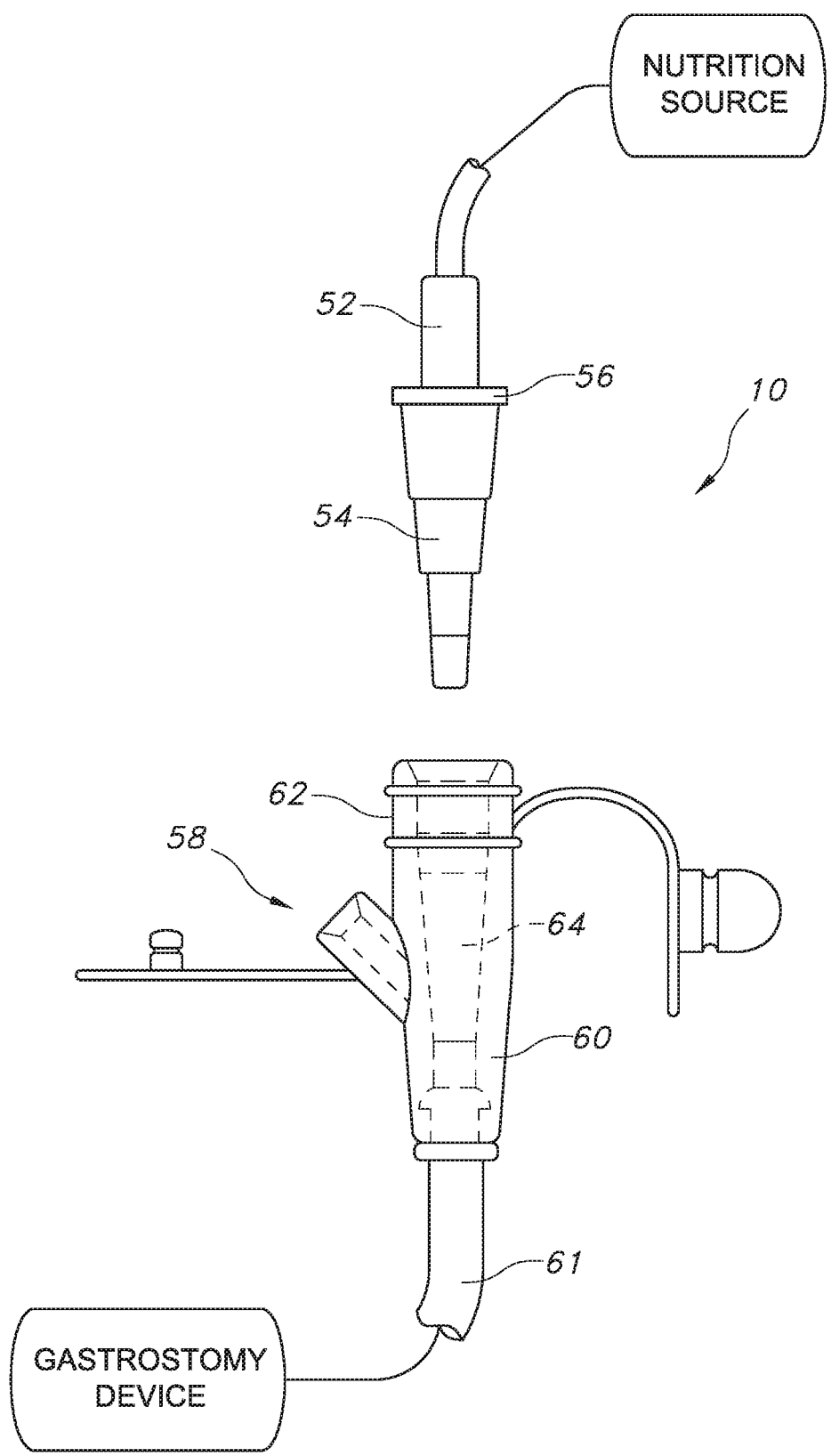
FIG. 1 is partial component view of an exemplary enteral feeding system.

Repeat use of reference characters in the present specification and drawings is intended to represent the same or analogous features or elements of the present invention.

DETAILED DESCRIPTION

Reference will now be made in detail to embodiments of the present invention, examples of which are illustrated in the figures. Each embodiment is provided by way of explanation of the invention and is not meant as a limitation of the invention. For example, features illustrated or described as part of one embodiment may be used with another embodiment to yield still a further embodiment. It is intended that the present invention include these and other modifications and variations coming within the scope and spirit of the invention.

Generally speaking, the present invention is directed to a single-use, tamper proof in-line connector for a feeding system, such as an enteral feeding system. The in-line connector includes a first component that is inserted into a second component, wherein a releasable locking mechanism (e.g., tabs located on an outer surface of the first component and corresponding indentations located on the second component interior wall) is provided to prevent the first component and the second component from rotating when connected. The in-line connector further includes one or more prongs positioned substantially flush against an interior wall of the second component when the first component and the second component are connected such that the prongs do not interfere with the releasable locking mechanism. Meanwhile, the one or more prongs are displaced away from the interior wall and into a recess defined by the interior wall when the first component is detached or disconnected from the second component via the releasable locking mechanism. For instance, the prongs can be spring-loaded or formed from a material that can release from the interior wall when the connection between the first component and the second component of the connector is broken such that the second component resists reconnection, reinsertion, or reattachment of the first component. Specifically, when released from the interior wall, the prongs can fold, bend, or collapse into the recess such that the prongs can be curved and point toward the upper end of the second component. In this manner, the prongs can have a curvilinear shape to prevent re-use of a disconnected connector due to the resistance to reinsertion that exists when the prongs are in a folded, bent, or collapsed position. For purposes of the present invention, it is contemplated that the terms "prong" or "prongs" are not limited to discrete finger-like structures, spines, tines, or limbs but may include elements that are compressed, deformed, or displaced to a first position (on or within one component) when one component is initially joined to the other component to allow the first and second components to join and subsequently expand, decompress, revert, or return to a second position when the connection between the first component and the second component of the connector is broken such that the two components resist reconnection, reinsertion, or reattachment.

FIG. 1 is a representation of an enteral feeding system 10 that is conventionally utilized to provide nutrition to a patient. The system 10 includes a first feeding device 50 that is in communication with a nutritional solution source. In this particular embodiment, the first feeding device 50 incorporates a feeding tube 52 mated with a connector element 54. Connector element 54 can include any manner of support structure, such as a flange 56, and may include a stepped-tapered end or screw connection mechanism for engagement into a second feeding device 58. In the illustrated embodiment, the second feeding device 58 is a conventional feeding adaptor 60 having an outer circumferential wall 62 defining an inner stepped channel 64 into which the tapered end of the connector element 54 is inserted. A tube 61 connects the adaptor 60 to a gastrostomy device that is implanted in the patient. The construction and operation of enteral feeding systems incorporating any manner of connectable feeding devices between a nutritional source and a patient gastrostomy device are well known and understood in the art, and a detailed explanation thereof is not necessary for purposes of the present disclosure.

It should also be readily appreciated that the first feeding device 50 and second device 58 illustrated in FIG. 1 are exemplary types of feeding devices that may be used in an enteral feeding system 10, and such devices are not a limitation of the scope and use of a connector 12 in accordance with aspects of the invention.

Figures 2A, 2B:
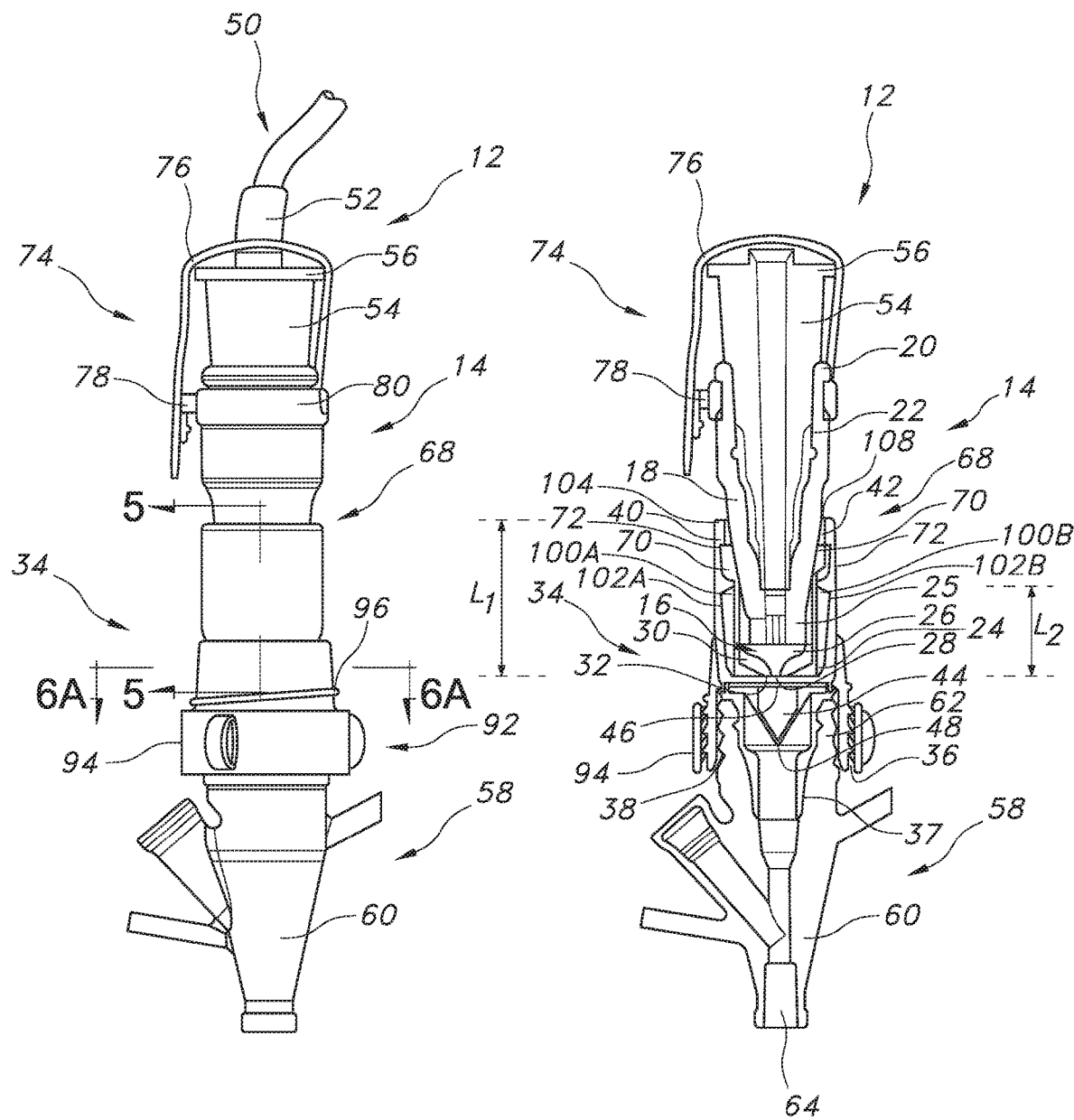
FIG. 2A is an exterior perspective view of an embodiment of a connector in accordance with aspects of the invention for use as an in-line component of an enteral feeding system in a connected state.
FIG. 2B is an interior cross-sectional view of the connector of FIG. 2A in a connected state.
Figure 4A:
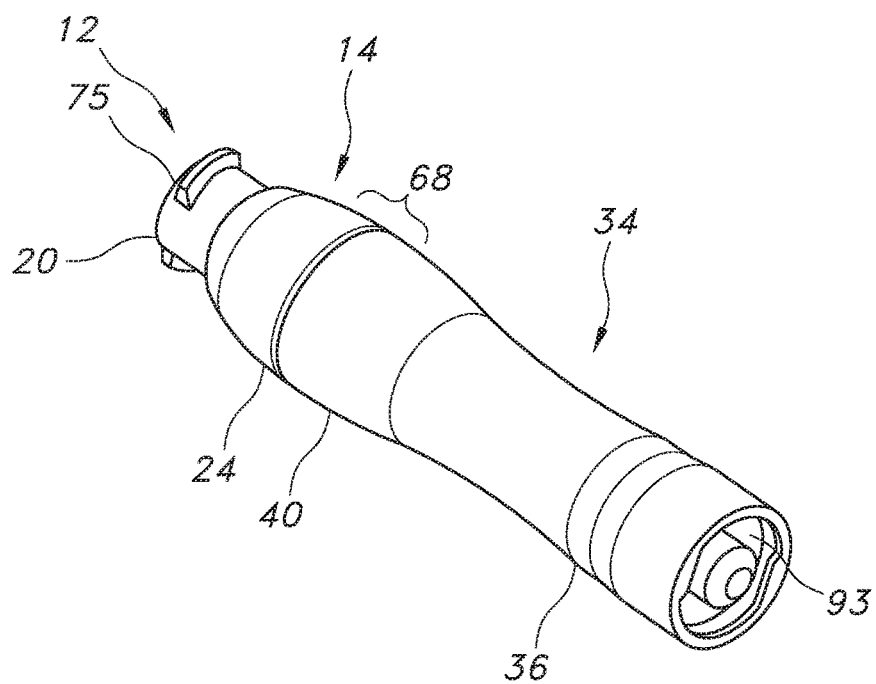
FIGS. 4A and 4B are perspective views of the components of the connector of FIGS. 2A and 2B in a connected and disconnected state, respectively.
Figure 4B:
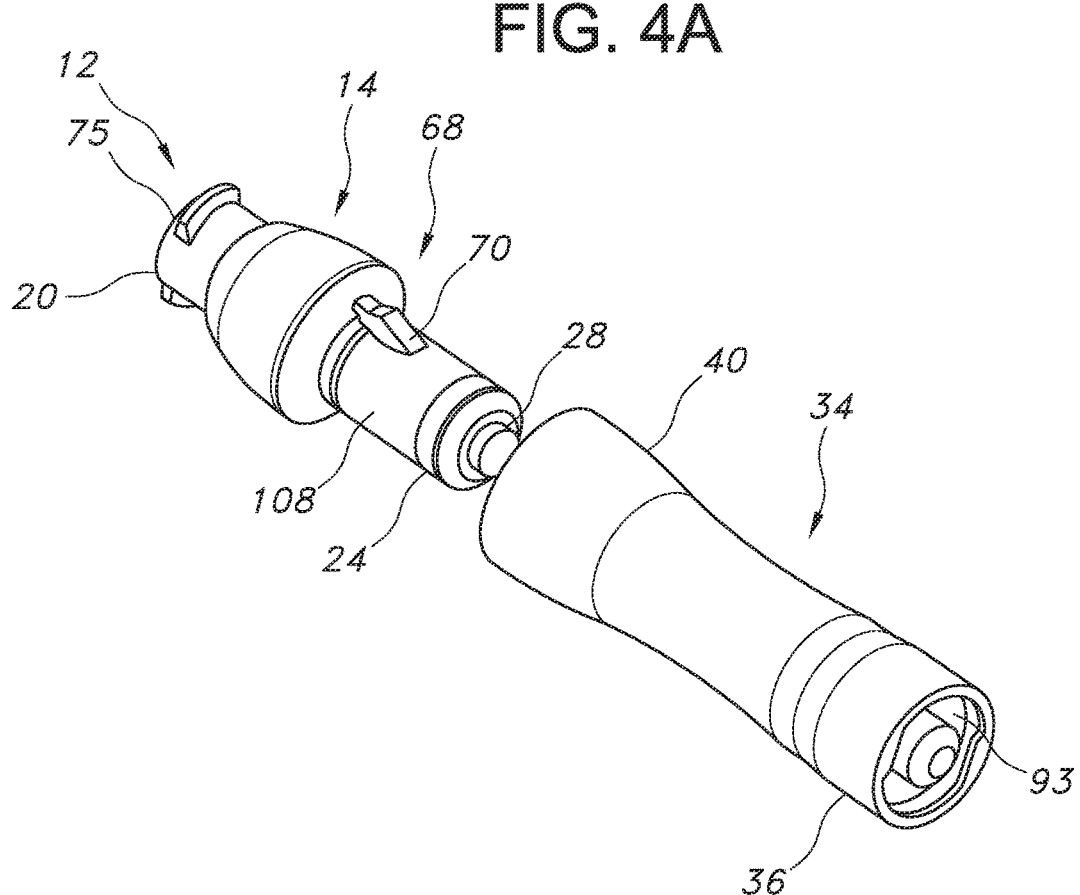

FIGS. 2A and 2B illustrate a particular embodiment of a connector 12 in accordance with aspects of the invention. FIG. 4A is an assembled or connected component view of the connector 12, while FIG. 4B is a disassembled or disconnected component view of the connector 12. Referring to FIGS. 2A, 2B, 4A, and 4B, the connector 12 includes a first component 14 that is connectable to the first feeding device 50, in particular to the connector element 54. The connector 12 also includes a second component 34 that is connectable to the second feeding device 58, in particular to the feeding adaptor 60. A releasable locking mechanism, generally 68, is configured between the first component 14 and second component 34. In the illustrated embodiment, this locking mechanism 68 is defined by a configuration wherein one or more tabs 70 are provided on or adjacent a lower end 24 of the first component 14 on its outer surface 108 (see FIG. 4B) engage within one or more correspondingly shaped indentations 72 (see FIG. 2B) present on the interior wall 104 of the second component 34 at its upper end 40. This configuration ensures that the components remain securely connected in operation of the connector 12 and do not rotate during use, but still allows the first and second components to be manually pulled apart and disconnected. It should be readily appreciated that in addition to the tab 70 and indentation 72 configuration discussed above, any manner of conventional releasable coupling devices/locking mechanisms may be used to connect the first and second components together (e.g., detents and corresponding grooves, etc.). In the connected state of the first component 14 and the second component 34 illustrated, for example, in FIG. 2A, the components define a fluid passage between the first feeding device 50 and second feeding device 58.

Referring now to FIG. 2B, each of the first component 14 and the second component 34 can also include an automatic shut-off valve. For example, the first component 14 includes a shut-off valve 16 that prevents flow of the nutritional solution out of the first component 14 in a first direction.

Meanwhile, the second component 34 includes a shut-off valve 44 that prevents back flow of nutritional solution and other gastric juices from leaking out of the second component 34 in a disconnected state of the connector 12.

It should be readily appreciated that the individual types of shut-off valves in the first component 14 and the second component 34 are not limited to the types of valves illustrated and discussed herein. Any number of valves that allow flow in one direction, yet prevent flow in an opposite direction, or only allow fluid flow upon being actuated to an open position, are known in the art and any configuration of such valves may prove useful in the connector 12 according to the present invention.

In the illustrated embodiment, the first component 14 includes an elongated body 18 having an upper (first) cylindrical end 20 that is configured for receipt of the first feeding device 50, such as the feeding tube 52 and connector element 54, within a recess 22. The first component 14 may include a lower (second) generally cylindrical end 24 that engages within the cylindrical recess 42 defined in the upper (second) end 40 of the second component 34 by way of the releasable coupling 68, as discussed above and particularly illustrated in FIG. 2B. The second component 34 includes a lower (first) end 36 that engages with the second feeding device 58, in particular with the feeding adaptor 60.

The shut-off valve 44 in the second component 34 may be any conventional type of check valve that allows fluid flow in a first direction, yet prevents flow in an opposite second direction. In the illustrated embodiment, the shut-off valve 44 is defined by a conventional resilient-flap valve referred to in the art as a "duckbill" valve seated within a chamber 48. It should be readily appreciated that any type of check valve may be utilized in this regard.

Referring to FIGS. 2B, 4A, and 4B, the second component 34 includes a recess 38 defined in the lower end 36 for receipt of wall 62 of the feeding adaptor 60. A conically shaped tip 37 is concentric within the recess 38 and frictionally engages within the tapered channel 64 within the feeding adaptor 60, as particularly illustrated in FIG. 2B.

Figure 3A:
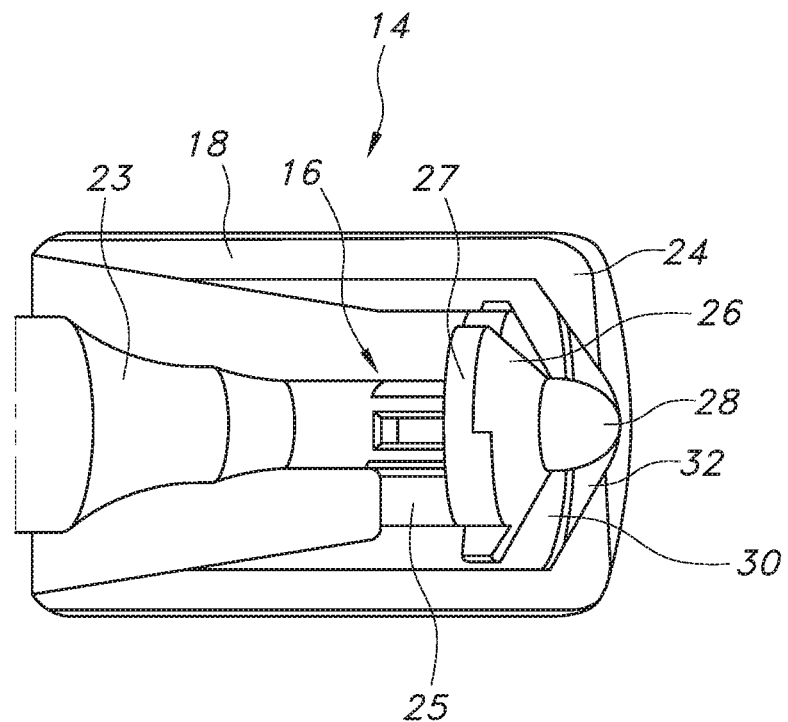
FIGS. 3A and 3B are cross-sectional operational views of the first component of the connector of FIGS. 2A and 2B.
Figure 3B:
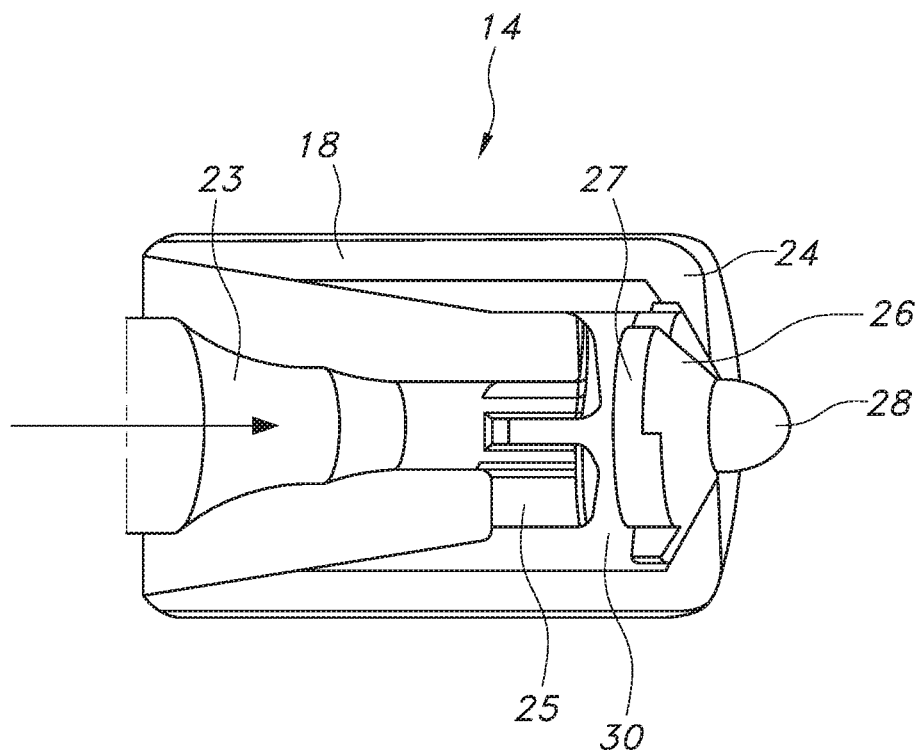

Referring particularly to FIGS. 2B, 3A, and 3B, the shut-off valve 16 in the illustrated embodiment includes a member that is engaged and moved to an open position by engagement of the first component 14 with the second component 34. For example, referring particularly to FIGS. 3A and 3B, the shut-off valve 16 includes a tapered plug member 26 that "floats" within a tapered chamber 30. An opening 32 in the lower end 24 of the first component 14 provides access out of the chamber 30. The plug member 26 includes a number of circumferentially spaced tabs 27 therearound that provide for alignment and stability of the plug member 26 within the chamber 30. A protruding nub 28 is defined in the center of the tapered plug 26. The nub 28 extends through the opening 32 in a sealed position of the valve 16 as illustrated in FIG. 3B. Fluid flow from the nutritional source is conveyed through the channel 23 in the first component 14 and is directed into the chamber 30 through the circumferentially spaced cage members 25. In a disconnected state of the first component 14, this fluid flow causes the plug 26 to seat against the tapered walls of the chamber 30, thus sealing the opening 32 and preventing the fluid from leaking out of the first component 14. When the first component 14 is engaged into the second component 34, as illustrated in FIG. 2B, a structural component within the second component 34 engages the nub 28 and presses the plug 26 into the chamber 30 against the end of the cage members 25, as illustrated in FIG. 3A. In this position of the tapered plug 26, fluid is free to travel through the channel 23, out through the cage members 25 and into the chamber 30, around the tabs 27 on the plug 26, and out through the opening 32 and into the second component 34. In the illustrated embodiment, the structural element within the second component 34 which engages the nub 28 is a perforated plate member 46. This plate 46 may be, for example, a sieve plate, or any other type of perforated plate that allows fluid flow therethrough. In an alternative embodiment, the engaging component may be a pin or any other type of structure that is positioned to engage the nub 28.

Thus, in summary, in the connected configuration of the first component 14 and second component 34 in the embodiment illustrated in FIGS. 2A and 2B, fluid from the nutritional source is directed through the first feeding device 50 and into the channel 23. The fluid is directed from the channel through the cage members 25 and into the chamber 30. In the engaged configuration of the components 14, 34, the plug 26 is unseated from the tapered walls of the chamber 30 and is backseated against the cage members 25. In this position of the plug 26, fluid is free to travel around the plug and exit through the opening 32. The fluid passes through the sieve or perforations in the engaging plate 46 and through the duckbill valve 44 in the second component 34. The fluid pressure opens the duckbill valve 44, and the nutritional fluid is allowed to pass into the feeding adaptor 60.

In the disconnected state of the first component 14 and the second component 34, as illustrated in FIG. 4, the duckbill valve 44 prevents backflow leakage of the nutritional fluid and any other gastric juices from the adaptor 60. Positive fluid pressure within the first component 14 causes the tapered plug 26 to assume the sealed position illustrated in FIG. 3B, thus preventing any leakage of the nutritional fluid from the first feeding device 50 through the first component 14. As previously mentioned, closure of the tapered plug 26 upon an inadvertent disconnection of the first and second components may result in an alarm condition at the feed source. This alarm will notify the caregiver of an abnormal condition, wherein the connector can be immediately reconnected without significant disruption of the nutritional solution to the patient.

It may be desirable to include any manner of coupling mechanism with either of the first component 14 or the second component 34 to insure that the components stay engaged with their respective feeding devices 50 and 58. In the embodiment of FIGS. 2A and 2B, a clamping mechanism 74 is provided in the form of a zip-tie configuration wherein zip-tie connector elements 76 engage on either side of the feeding tube connector 54 of the first feeding device 50, as illustrated in FIG. 2A, and are secured by a releasable clamp 78. The zip-tie elements 76 and latches 78 may be contained on a band 80 that fits onto the upper end 20 of the first component 14. The zip-tie elements 76 pull the flange 56 of the connector element 54 into engagement within the recess in the first component 14 and ensure that the connector element 54 cannot be inadvertently pulled from the first component 14.

The embodiment of FIGS. 4A and 4B illustrates a second type of coupling mechanism that can be in the form of a screw connection mechanism 75. Although not shown in FIGS. 4A and 4B, the screw connection mechanism 75 includes threads similar to those shown for screw connection mechanism 93 discussed in more detail below with respect to the second component 34. In any event, the screw connection mechanism 75 can be used to connect the first component 14 to the first feeding device 50, which can have corresponding grooves formed therein.

It may also be desired to include any manner of conventional coupling mechanism such as a clamping mechanism 92 or screw connection mechanism 93 on the second component 34. Again, it should be readily appreciated that any manner of conventional connecting or clamping device may be utilized in this regard. In the illustrated embodiment as shown in FIGS. 2A and 2B, the coupling mechanism is in the form of a second clamping mechanism 92, where a compression ring 94 is threadedly engaged on body threads 96 of the second component 34, as particularly illustrated in FIG. 2B. Threaded advancement of the compression ring 94 towards the lower end 36 of the second component 34 causes the circumferential wall of the component 34 to radially compress onto the circumferential wall 62 of the feeding adaptor 60 of the second feeding device 58 that is inserted within the recess 38 in the end of the second component 34. To release the component 34 from the adaptor 60, the compression ring 94 is simply rotated in the opposite direction to release the compressive force. However, it is to be understood that any suitable coupling mechanism, such as a screw connection mechanism 93, can also be utilized with respect to the second component 34. For instance, as shown in FIGS. 4A and 4B, the screw connection mechanism 93 includes threads that can be used to attach the second component 34 with a feeding adaptor 60, which can have corresponding grooves formed therein (see FIGS. 1, 2A, and 2B).

As mentioned above, the in-line connector 12 also includes a releasable locking mechanism 68 configured between the lower end 24 of the first component 14 and the upper end 40 of the second component 34 where, when engaged, the locking mechanism 68 facilitates a connected state between the first component 14 and the second component 34 to define a fluid passage between the first feeding device 50 and the second feeding device 58 and also prevents rotation of the first component 14 and the second component 34. However, once the first component 14 is disconnected from the second component 34, the in-line connector 12 should not be re-used, and there is a need for preventing a user from engaging the first component 14 and the second component 34 via the locking mechanism 68. As such, the in-line connector 12 of the present invention includes one or more movable prongs 100A-100D, as shown in FIGS. 2B, 5, 6A, and 6B.

Figure 5:
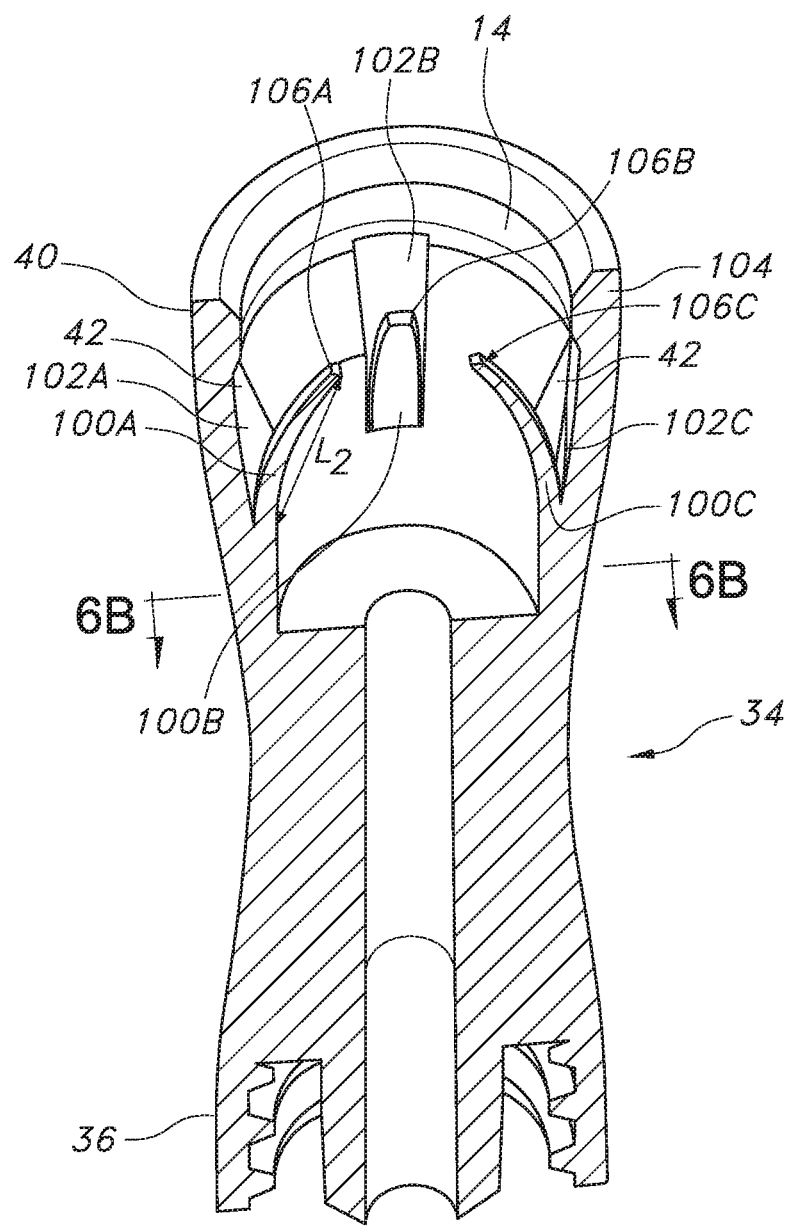
FIG. 5 is an interior perspective view of the second component of the connector of FIG. 2B when the first component is disconnected from the second component at cut line 5-5 in FIG. 2A.
Figure 6A:
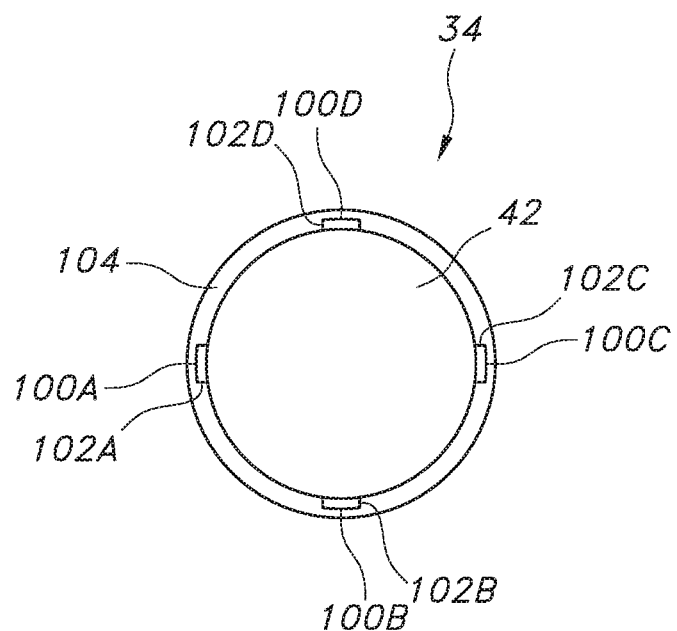
FIG. 6A is a top view of the second component at cut line 6A-6A in FIG. 2A when the first component is connected to the second component.
Figure 6B:
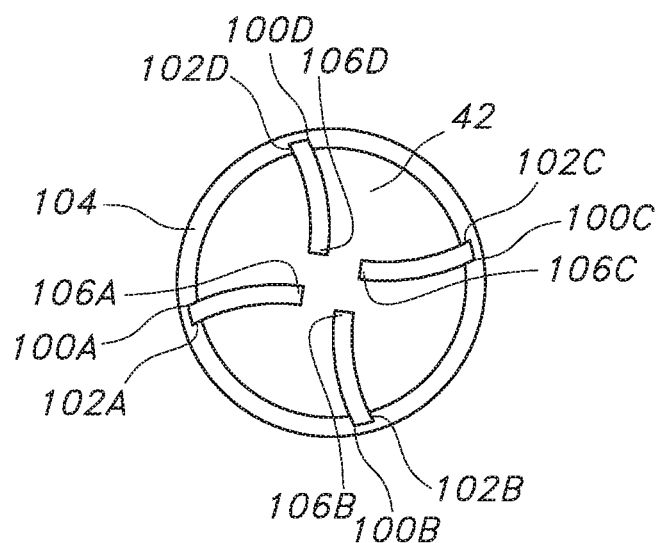
FIG. 6B is a top view of the second component at cut line 6B-6B in FIG. 5 after the first component has been disconnected or detached from the second component.

Any suitable number of prongs 100A-100D, etc. can be utilized, so long as the prongs do not interfere with the functionality of the locking mechanism 68 when it is desired to form a connection between the first component 14 and the second component 34. For instance, one, two, three, four, five, six, seven, eight, nine, or ten prongs can be utilized. Referring to FIGS. 2B and 6A, as the first component 14 is connected to the second component 34 of the connector 12 via locking mechanism 68, and after the first component 14 and the second component 34 are connected, the prongs, such as prongs 100A, 100B, 100C, and 100D, are substantially flush with the interior wall 104 of the second component 34. To this end, the prongs 100A, 100B, 100C, and 100D can be contained within pockets 102A, 102B, 102C, and 102D formed in the interior wall 104 that defines the recess 42 of the second component 34. As shown in FIGS. 5 and 6A, the pockets 102A-102D are discretely formed about the circumference of the interior wall 104 such that the pockets are each separated from one another. However, referring to FIGS. 5 and 6B, the prongs 100A, 100B, 100C, 100D, etc. are movable in that once the first component 14 is disconnected from the second component 34, the prongs are displaced away from the interior wall 104 and can be folded, bent, or collapsed into the recess 42. Once collapsed away from the interior wall 104, the prongs 100A, 100B, 100C, and 100D can be curvilinear as shown and can have tips 106A, 106B, 106C, and 100D that point towards a center of the recess 32 and towards an upper end 40 of the second component 34. In this manner, the prongs 100A, 100B, 100C, and 100D, in a collapsed state, can prevent the first component 14 from being reconnected with the second component 34 via the locking mechanism 68.

However, it is to be understood that the prongs should not interfere with the locking mechanism 68 during use of the in-line connector so that an adequate connection can be formed between the first component 14 and the second component 34 to prevent rotation of the in-line connector 12 during use. As such and referring to FIG. 2B, the prongs, such as prongs 100A and 100B in FIG. 2B, have a length L2 that is less than a length L1 of the recess 42. In this manner, there is still sufficient space in the interior wall 104 of the second component 34 for indentations 72 to receive corresponding tabs 70 positioned on an outer surface 108 of the first component 14 to form the locking mechanism 68 that prevents rotation of the connector 12 during use, where the prongs 100A, 100B, 100C, 100D, etc. are positioned beneath the indentations 72 and towards the lower end 36 of the second component 34 and the indentations 72 are positioned above the prongs 100A, 100B, 100C, 100D, etc. and towards an upper end 40 of the second component 34.

In order to facilitate the displacement of the prongs 100A, 100B, 100C, 100D, etc. away from the interior wall 104 when the first component 14 is disconnected from the second component 34, the prongs 100A, 100B, 100C, 100D, etc. can be formed from a flexible material that can be displaced upon removal of the first component 14 from the second component 34, where the material is not so rigid that it is easily breakable but is not so soft so that it can maintain in position and resist reconnection of the first component 14 with the second component 34. For instance, the prongs 100A, 100B, 100C, 100D, 100C, etc. can be formed from polyacetal, polycarbonate, acrylonitrile butadiene styrene, or a combination thereof. Alternatively or in addition forming the prongs 100A, 100B, 100C, 100D, etc. from the aforementioned materials, the prongs 100A, 100B, 100C, 100D, etc. can be spring-loaded. In any event, regardless of the specific mechanism by which the prongs 100A, 100B, 100C, 100D, etc. are displaced away from the interior wall 104 of the second component 34 after disconnection of the first component 14 from the second component 34, the prongs prevent reconnection of the first component 14 and the second component 34 after the first component 14 and the second component 34 are in a disconnected state by blocking the first component 14 from being sufficiently inserted into the second component 34 to engage its tabs 70 with the indentations 72 formed in the interior wall 104 of the second component 34.

Moreover, because the prongs 100A, 100B, 100C, and 100D may be molded in their collapsed or displaced position, there may be a tendency for the prongs 100A, 100B, 100C, 100D, etc. to displace away from the interior wall 104 before a connection is made between the first component 14 and the second component 34 during assembly of the connector 12 via locking means 68, a tool can be used to hold the prongs 100A, 100B, 100C, 100D, etc. substantially flush against the interior wall 104 of the second component 34 during the initial connection.

As noted previously, it is contemplated that "prong" or "prongs" are not limited to discrete finger-like structures, spines, tines, or limbs but may include elements that are compressed, deformed or displaced to a first position (within one component—e.g., the second component) when the other component (e.g., the first component) is initially joined to the second component to allow the first and second components to join and subsequently expand, decompress, revert or return to a second position when the connection between the first component and the second component of the connector is broken such that the two components resist reconnection, reinsertion, or reattachment. Exemplary embodiments include compressible materials, springs, compressible sponge or sponge-like materials that expand or revert to prevent reinsertion; deformable bands, films or film-like elements, strings, webs or web-like elements that initially separate and then revert to prevent reinsertion; flexible annular rings, annular springs, or the like that contract radially to prevent reinsertion and combinations of the above.

It should be readily appreciated that the invention also encompasses use of one or more of the connectors 12 in accordance with the invention as an in-line component within any manner of conventional enteral feeding system 10.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An in-line connector for use in an enteral feeding system, the in-line connector comprising:
    a first component connectable to a first feeding device of the feeding system and having an upper end and a lower end;
    a second component connectable to a second feeding device of the feeding system and having an upper end and a lower end; and
    a releasable locking mechanism configured between the lower end of the first component and the upper end of the second component, wherein in a connected state the first component and the second component define a fluid passage between the first and second feeding devices;
    wherein an interior wall of the second component defines a recess for receiving the first component, wherein the interior wall includes movable prongs that are substantially flush with the interior wall when the first component and the second component are in a connected state, and wherein the prongs are displaced away from the interior wall when the first component and the second component are in a disconnected state, and further wherein the prongs sit in a plurality of corresponding discrete pockets formed in the interior wall when the first component and the second component are in a connected state so that the prongs are flush with the interior wall when the first component and the second component are in the connected state.

2. The in-line connector of claim 1, wherein the prongs are curvilinear when the first component and second component are in a disconnected state.

3. The in-line connector of claim 2, wherein a tip of each of the prongs curves towards the upper end of the second component when the first component and second component are in a disconnected state.

4. The in-line connector of claim 1, wherein the prongs have a length that is less than a length of the interior wall.

5. The in-line connector of claim 1, wherein the prongs are formed from polyacetal, polycarbonate, acrylonitrile butadiene styrene, co-polyester or a combination thereof.

6. The in-line connector of claim 1, wherein the prongs are spring-loaded.

7. The in-line connector of claim 1, wherein the prongs prevent reconnection of the first component and the second component after the first component and the second component are in a disconnected state.

8. The in-line connector of claim 1, wherein the in-line connector is single use.

9. The in-line connector of claim 1, wherein the releasable locking mechanism comprises tabs present on an outer surface of the first component and corresponding indentations present on the interior wall of the second component.

10. The in-line connector of claim 9, wherein the prongs are positioned beneath the indentations and towards the lower end of the second component.

11. The in-line connector of claim 9, wherein the indentations are positioned above the prongs and towards an upper end of the second component.

12. The in-line connector of claim 1, wherein the first component comprises an elongated body, wherein the upper end of the first component is configured for receipt of a feeding tube therein and the lower end of the second component is generally cylindrical, further wherein the lower end of the second component is configured for receipt of a feeding adapter therein and the upper end of the first component defines a cylindrical recess for receipt of the lower end of the first component.

13. The in-line connector of claim 1, wherein the first component and the second component each further comprise an automatic shutoff valve configured therein such that in a disconnected state of the first component and the second component, the shutoff valve in the first component prevents flow out of the first component in a first direction and the shutoff valve in the second component prevents flow out of the second component in a second direction that is opposite from the first direction, wherein the shutoff valve in the first component is engaged and moved to an open position by a component in the second end of the second component upon connecting the first component and the second component together.

14. The in-line connector of claim 13, wherein the shutoff valve in the first component comprises a tapered plug member movable within a tapered chamber, the plug member further comprising an engagement nub extending through an opening in the lower end of the first component, wherein the nub is engaged by a component in the upper end of the second component to move the plug to an open position of the shutoff valve.

15. The in-line connector of claim 14, wherein the plug member is moved to a sealed position within the chamber by fluid flow through the first component in the first direction.

16. The in-line connector of claim 13, wherein the shutoff valve in the second component is biased to a closed position against flow through the second component in the second direction and is opened by fluid flow through the second component in the first direction.

17. The in-line connector of claim 1, further comprising a clamping mechanism or screw connection mechanism on the first component configured to releasably attach the first component to the first feeding device and a clamping mechanism or screw connection mechanism on the second component configured to releasably attach the second component to the second feeding device.

18. An in-line connector for use in an enteral feeding system, the in-line connector comprising:
   a first component connectable to a first feeding device of the feeding system and having an upper end and a lower end;
   a second component connectable to a second feeding device of the feeding system and having an upper end and a lower end; and
   a releasable locking mechanism configured between the lower end of the first component and the upper end of the second component, wherein in a connected state the first component and the second component define a fluid passage between the first and second feeding devices;
   wherein an interior wall of the second component defines a recess for receiving the first component, wherein the interior wall includes one or more movable elements that are substantially flush with the interior wall when the first component and the second component are in a connected state, wherein the one or more movable elements are displaced away from the interior wall when the first component and the second component are in a disconnected state, and further wherein the one or more movable elements sit in in a plurality of corresponding discrete pockets formed in the interior wall when the first component and the second component are in a connected state so that the one or more movable elements are flush with the interior wall when the first component and the second component are in the connected state.

19. The in-line connector of claim 18, wherein the one or more moveable elements include compressible materials, springs, compressible sponges; deformable bands, films, strings, webs; flexible annular rings, annular springs and combinations of the above.

* * * * *